United States Patent [19]

Hudspeth et al.

[11] Patent Number: 5,034,512

[45] Date of Patent: Jul. 23, 1991

[54] BRANCHED BACKBONE RENIN INHIBITORS

[75] Inventors: James P. Hudspeth, Newbury Park, Calif.; James S. Kaltenbronn, Ann Arbor, Mich.; Joseph T. Repine, Ann Arbor, Mich.; Ila Sircar, Ann Arbor, Mich.

[73] Assignee: Warner-Lambert Company, Morris Plains, N.J.

[21] Appl. No.: 226,873

[22] Filed: Aug. 3, 1988

Related U.S. Application Data

[63] Continuation-in-part of Ser. No. 112,578, Oct. 22, 1987, abandoned.

[51] Int. Cl.$^5$ .......................... C07K 5/08; C07K 5/10
[52] U.S. Cl. ................................. 530/330; 530/331; 530/332
[58] Field of Search ................... 514/19, 18; 530/330, 530/331, 332

[56] References Cited

U.S. PATENT DOCUMENTS 4,839,357  6/1989  Patchett et al. ................ 514/235.8

OTHER PUBLICATIONS

Burger, *Medicinal Chemistry*, 1960, pp. 565–571, 578–581, 600–601.
Denkewalter et al., *Progress In Drug Research*, 1966, pp. 510–512.
Plattner et al., *J. Med. Chem.*, 1988, 31(12), pp. 2277–2288.

*Primary Examiner*—Lester L. Lee
*Assistant Examiner*—Stephen B. Maebius
*Attorney, Agent, or Firm*—Elizabeth M. Anderson

[57] ABSTRACT

The invention concerns a novel series of renin-inhibitory branched-backbone peptides which are useful for treating renin associated hypertension, congestive heart failure, and hyperaldosteronism. Processes for preparing the peptides, compositions containing them and methods of using them are included. Also included is a diagnostic test using the compounds to determine the presence of renin-associated hypertension, congestive heart failure, or hyperaldosteronism.

1 Claim, No Drawings

BRANCHED BACKBONE RENIN INHIBITORS

CROSS-REFERENCE TO RELATED APPLICATION

This is a continuation-in-part of United States application Ser. No. 112,578 filed Oct. 22, 1987 now abandoned.

BACKGROUND OF THE INVENTION

Renin is a natural enzyme which is released into the blood from the kidney. It cleaves its natural substrate, angiotensinogen, releasing a decapeptide, angiotensin I. This is in turn cleaved by converting enzyme in the lung, kidney and other tissues to an octapeptide, angiotensin II. Angiotensin II raises blood pressure both directly by causing arteriolar constriction and indirectly by stimulating release of the sodium-retaining hormone aldosterone from the adrenal gland causing a rise in extracellular fluid volume. Inhibitors of renins have been sought as an agent for control of hypertension, congestive heart failure, and hyperaldosteronism.

The present invention concerns a novel series of branched-backbone peptides which inhibit renin. It also concerns pharmaceutical compositions containing these novel peptides, methods of treating renin-associated hypertension, congestive heart failure, and hyperaldosteronism, as well as the use of the peptides as diagnostic tools, and the methods for preparing the peptides.

SUMMARY OF THE INVENTION

The present invention relates to novel peptides of the formula

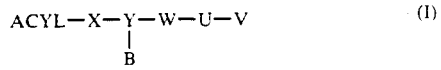

and the pharmaceutically acceptable acid addition salts thereof wherein ACYL, X, Y, W, U, V and B are as defined herein below.

The invention also includes pharmaceutical compositions comprising an effective amount of the above peptide of formula I in admixture with a pharmaceutically acceptable carrier or excipient and a method for treating renin-associated hypertension in a patient suffering therefrom comprising administering to said patient the above pharmaceutical composition in unit dosage form.

Further the invention includes a pharmaceutical composition comprising an effective amount of a peptide of formula I above in admixture with a pharmaceutically acceptable carrier or excipient, and a method for treating hyperaldosteronism in a patient suffering therefrom comprising administering to said patient the above pharmaceutical composition in unit dosage form.

Also the invention includes a pharmaceutical composition comprising an effective amount of a peptide of formula I above in admixture with a pharmaceutically acceptable carrier or excipient, and a method for treating congestive heart failure in a patient suffering therefrom comprising administering to said patient the above pharmaceutical composition in unit dosage form.

The present invention also includes the use of peptides of formula I above as diagnostic tools for the identification of cases of hypertension due to renin excess.

The invention further includes methods for preparing peptides of formula I above.

DETAILED DESCRIPTION

The following table provides a dictionary of the terms used in the description of the invention.

TABLE I

| Abbreviated Designation | |
|---|---|
| | Amino Acid |
| HIS | L-Histidine |
| LEU | L-Leucine |
| STA | 4(S)-Amino-3(S)-hydroxy-6-methylheptanoic acid |
| PHSTA | 4(S)-Amino-3(S)-hydroxy-5-phenylpentanoic acid |
| CYSTA | 4(S)-Amino-3(S)-hydroxy-5-cyclohexanepentanoic acid |
| ILE | L-Isoleucine |
| N—MeLEU | N-Methylleucine |
| N—MeILE | N-Methylisoleucine |
| PHE | L-Phenylalanine |
| HOMOPHE | Homophenylalanine |
| NLE | Norleucine |
| VAL | L-Valine |
| NAPHTHYLALA | Naphthylalanine |
| CYCLOHEXYLALA | Cyclohexylalanine |
| TYR | L-Tyrosine |
| TYR(OMe) | L-Tyrosine, OMe ether |
| TRP | L-Tryptophan |
| ASP | L-Aspartic Acid |
| GLU | L-Glutamic Acid |
| LYS | L-Lysine |
| ORN | L-Ornithine |
| GLY | Glycine |
| N-MeGLY | N-Methylglycine |
| ALA | L-Alanine |
| β-ALA | 3-Aminopropionic Acid |
| MET(O₂) | L-Methionine sulfone |
| SER | L-Serine |
| MET | L-Methionine |
| TZC | 4-Thiazolidinecarboxylic Acid |
| TXC(O₂) | 4-Thiazolidinecarboxylic Acid Sulfone |
| PGL | L-Pyroglutamic Acid |
| ASTA | 3(RS), 4(S)-Diamino-6-methylheptanoic acid |
| ACYS | 3(RS), 4(S)-Diamino-5-cyclohexanepentanoic acid |
| CHSTA | 4(S)-Amino-3(S)-hydroxy-4-cyclohexanebutanoic acid |
| DFKSTA | 4(S)-Amino-3-oxo-2,2-difluoro-6-methylheptanoic acid |
| DFSTA | 4(S)-Amino-3(S)-hydroxy-2,2-difluoro-6-methylheptanoic acid |
| DFKCYS | 4(S)-Amino-3-oxo-2,2-difluoro-5-cyclohexanepentanoic acid |
| DFCYS | 4(S)-Amino-3-(S)-hydroxy-2,2-difluoro-5-cyclohexanepentanoic acid |
| DFKCHS | 4(S)-Amino-3-oxo-2,2-difluoro-4-cyclohexanebutanoic acid |
| DFCHS | 4(S)-Amino-3(S)-hydroxy-2,2-difluoro-4-cyclohexanebutanoic acid |
| | Acyl Group |
| DNMA | Di-(1-naphthylmethyl)acetyl |
| BOC | Tert-butyloxycarbonyl |
| Z | Benzyloxycarbonyl |
| IVA | Isovaleryl |
| NVA | n-Valeryl |
| BMA | 3-Amino-3-methylbutanoyl |
| BBSP | 2-Benzyl-3-(t-butylsulfonyl)propionyl |
| | Amides With |
| —NHCH₂Ph | Benzylamine |

TABLE I-continued

| Abbreviated Designation | | |
|---|---|---|
| 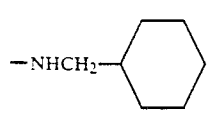 | Cyclohexylmethylamine | |
| 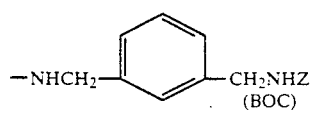 | m-Xylene-di-amine (Z or BOC) | |
| 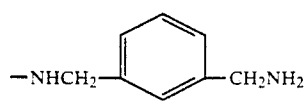 | m-Xylene-di-amine | |
|  | Ammonia | |
| 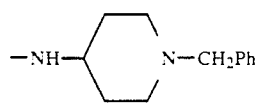 | 4-Amino-N-benzylpiperidine | |
| 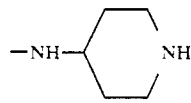 | 4-Aminopiperidine | |
| 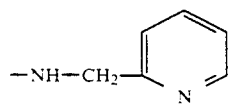 | 2-Aminomethylpyridine | |
| 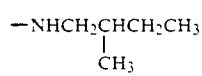 | 2-Methylbutylamine | |
| 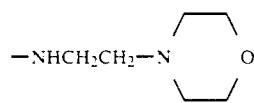 | N-(2-Aminoethyl)morpholine | |
| 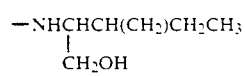 | 1-Hydroxymethyl-2-methylbutylamine | |
| | Esters With | |
| —OCH$_3$ | Methanol | |
| —OC$_2$H$_5$ | Ethanol | |
| —OCH(CH$_3$)$_2$ | Isopropanol | |
| | Solvents and Reagents | |
| DMF | N,N-Dimethylformamide | |
| HOBT | Hydroxybenzotriazole | |
| DCC | N,N'-Dicyclohexylcarbodiimide | |
| HOAc | Acetic Acid | |
| Et$_3$N | Triethylamine | |
| THF | Tetrahydrofuran | |
| TFA | Trifluoroacetic Acid | |
| MeOH | Methanol | |
| EtOAc | Ethyl Acetate | |
| Et$_2$O | Diethyl Ether | |

The term branched backbone refers to those compounds where, in addition to the α-amino group and the α-carboxyl group, a carboxyl or amino group in the side chain of an amino acid is also used to form peptide bonds, thus forming peptide chains that extend in more than one direction.

The peptides of the present invention are represented by the formula

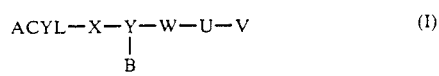

or pharmaceutically acceptable salts thereof, wherein
ACYL is BOC, Z, IVA, NVA, DNMA, BMA, BBSP,

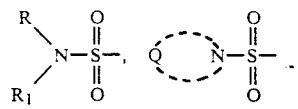

wherein R and R$_1$ are each independently hydrogen or straight or branched chain lower alkyl of from 1 to 4 carbon atoms,

is a saturated ring containing 2 to 5 carbon atoms wherein Q is CH$_2$, O, S, or NR, or

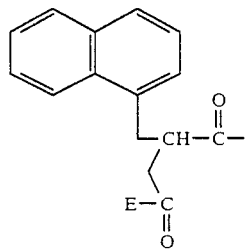

wherein E is N(CH$_3$)$_2$,

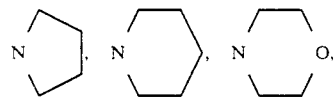

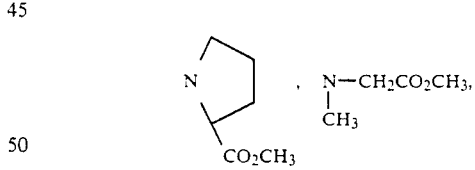

or OCH$_3$;
X is absent, PHE, HOMOPHE, NAPHTHYLALA, CYCLOHEXYLALA, TYR, TYR(OMe), or TRP with the proviso that when ACYL is DNMA, BBSP, or 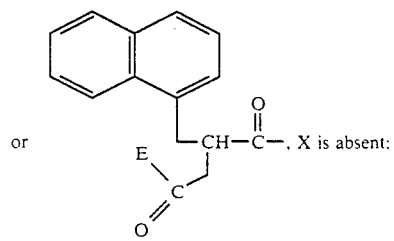, X is absent;

Y is ASP, GLU, LYS, ORN,

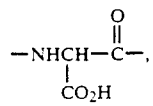

or another amino acid whose side chain terminates with an acidic or basic function such as:

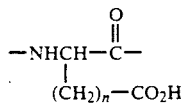

where n is 3-6, or

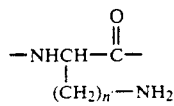

where n' is 1, 2, or 5-8;

B is $B_1$ or $B_2$; B is $B_1$ when Y is an acidic amino acid and the attachment of $B_1$ is through the amino portion of the amino acid and $B_1$ is GLY, N—MeGLY, ALA, β-ALA, HIS, MET($O_2$), LEU, ILE, NLE, PHE, SER and, where the amino acid carboxyl group of $B_1$ is present as a lower alkyl ester, amide, lower alkyl amide, lower dialkylamide, thioamide, lower alkyl thioamide, or lower dialkyl thioamide thereof;

B is $B_2$ or $B_2$; B is $B_1$ when Y is a basic amino acid and the attachment of $B_2$ is through the carboxyl portion of the amino acid and $B_2$ is GLY, ALA, β-ALA, LEU, NLE, ILE, TZC, TCZ, ($O_2$), PGL and the amino portion of $B_2$ is the free amine or acylated with

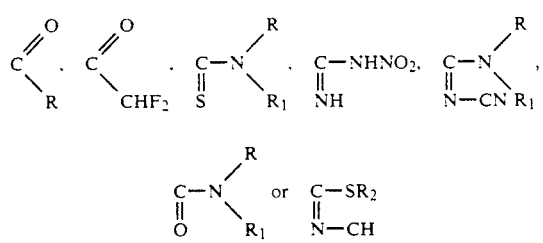

wherein R and $R_1$ are each independently hydrogen or a straight or branched chain lower alkyl of from one to four carbon atoms and $R_2$ is a lower alkyl of from one to four carbon atoms;

W is STA, CYSTA, PHSTA, ASTA, ACYS, CHSTA, DFKSTA, DFSTA, DFKCYS, DFCYS, DFKCHS, or DFCHS;

U is absent, LEU, ILE, VAL, PHE, N—MeLEU, or N—MeILE; and

V is $NHCH_2Ph$,

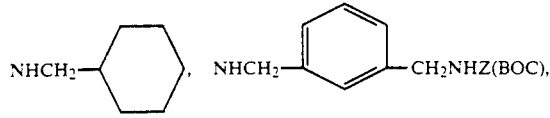

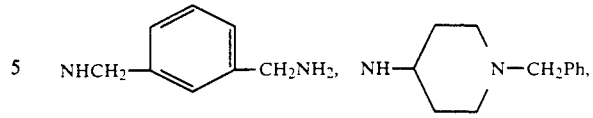

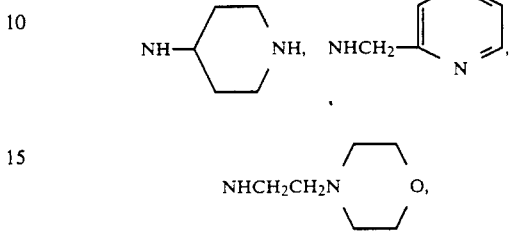

$NHCH_2CH(CH_3)CH_2CH_3$, $NHCHCH(CH_3)CH_2CH_3$
|
$CH_2OH$ $OCH_3$, $OC_2H_5$, or $OCH(CH_3)_2$.

Preferred compounds of the present invention are compounds of formula 1 wherein $B_1$ is GLY[CSNHCH₃], GLY—NHCH₃, MET($O_2$)OCH₃, HIS—OCH₃, β-ALA—NHCH₃, or β-ALA[CSNHCH₃] and $B_2$ is GLY, GLY(Z),

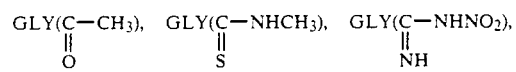

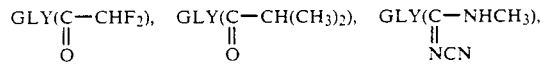

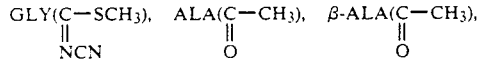

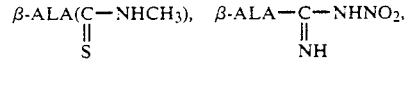

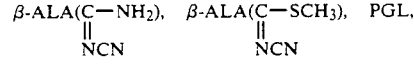

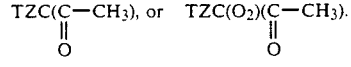

Other preferred compounds of the present invention are compounds of formula 1 wherein Y is ASP, GLU,

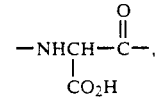

LYS, or ORN

V is $NHCH_2Ph$,

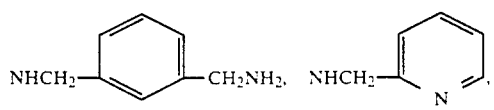 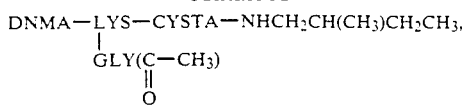
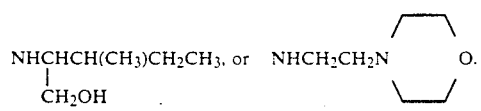 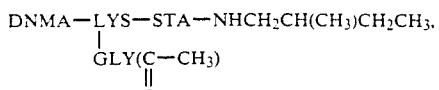
Particularly valuable compounds falling within the scope of the invention include the following compounds, their isomers, and pharmaceutically acceptable acid addition salts:
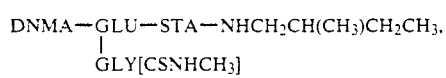 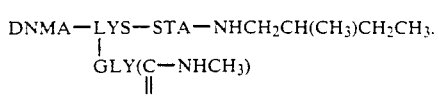
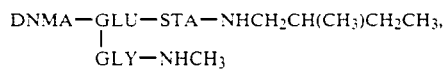 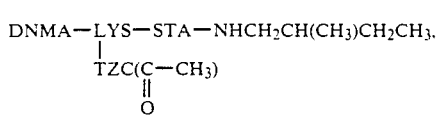
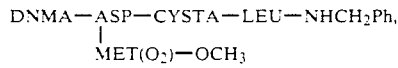 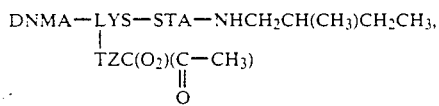
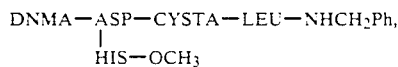 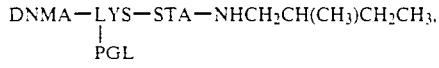
 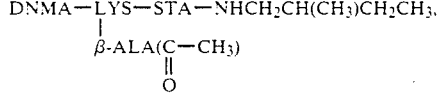
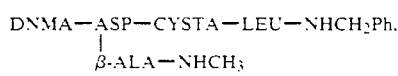 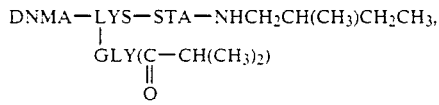
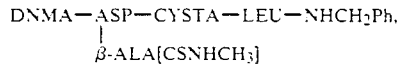 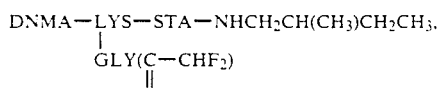
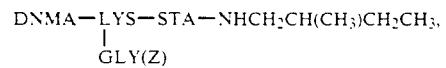 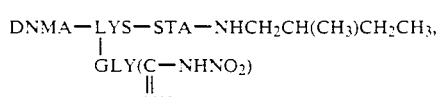
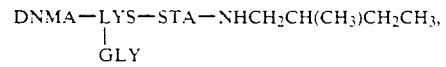 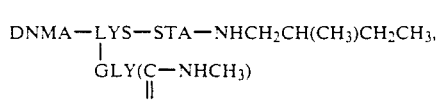
Other valuable compounds of the present invention include the following:
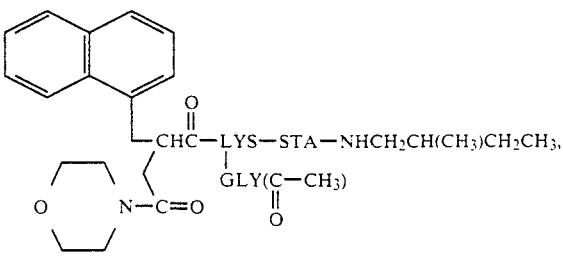

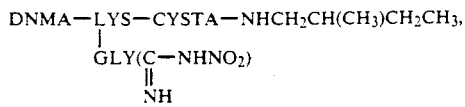
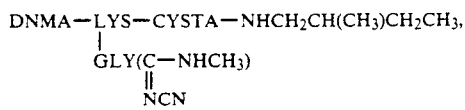
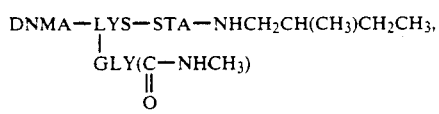
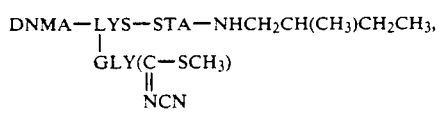
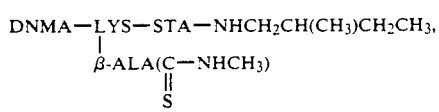
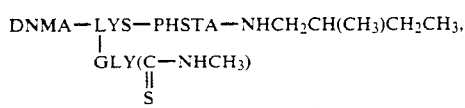
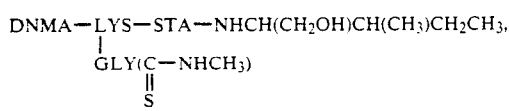
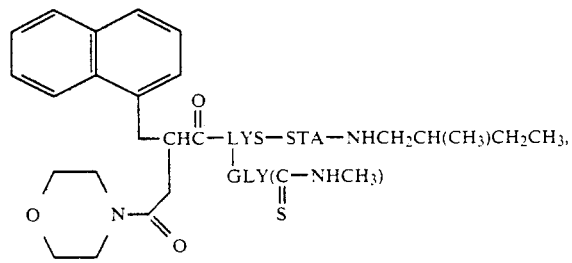
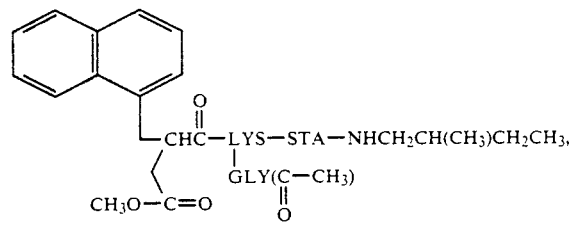
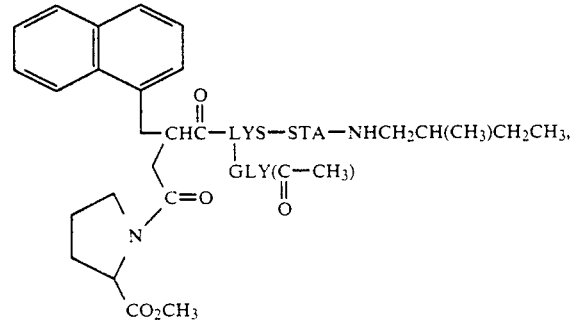

-continued
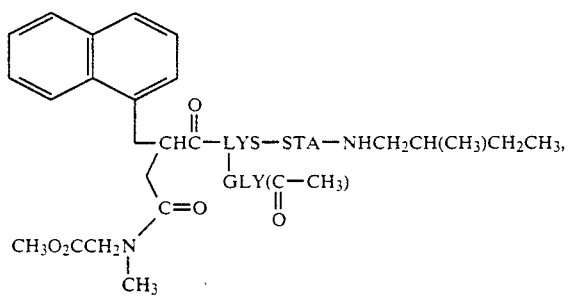
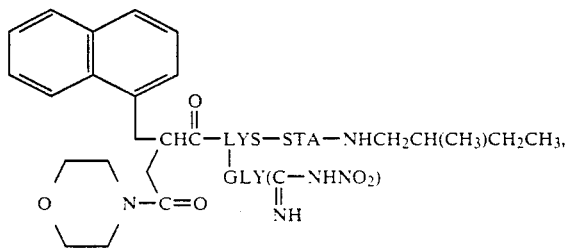
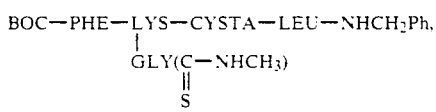
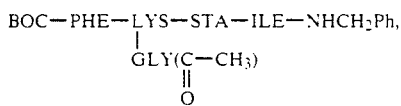
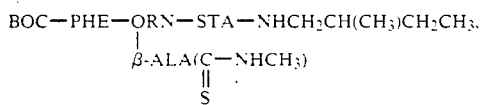
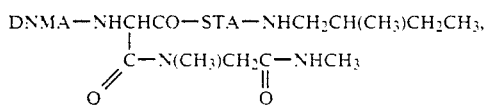
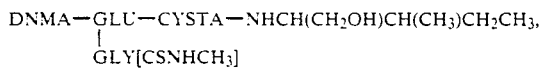
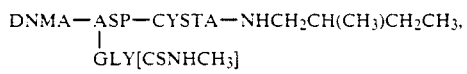
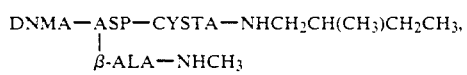
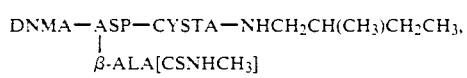
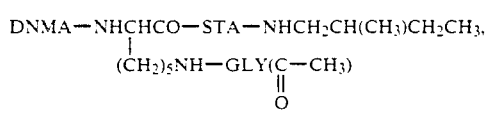

-continued
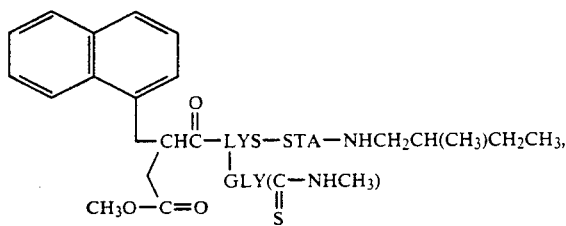
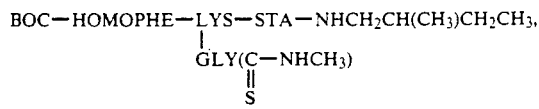
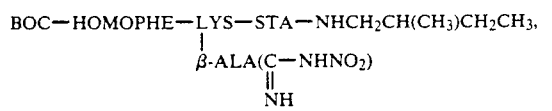
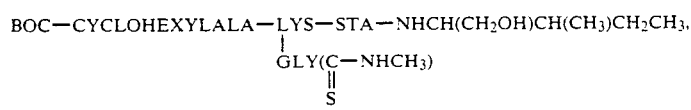
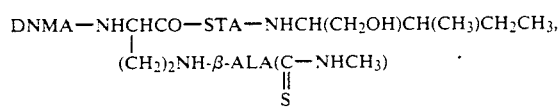
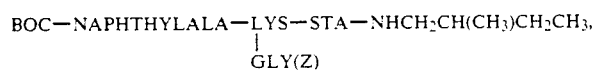
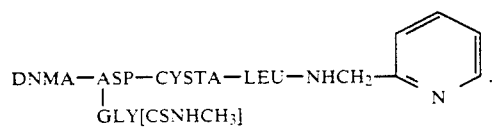
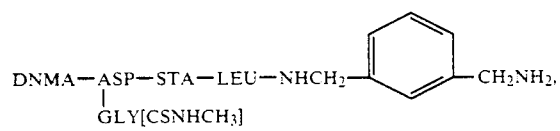
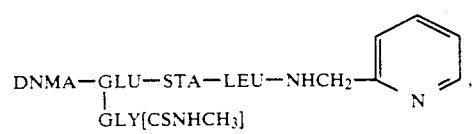
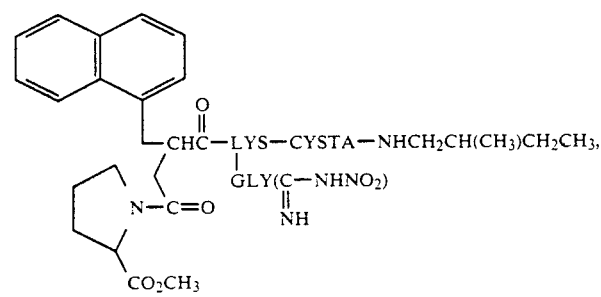
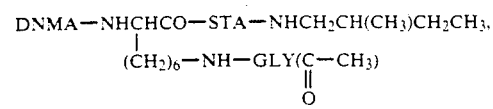

-continued
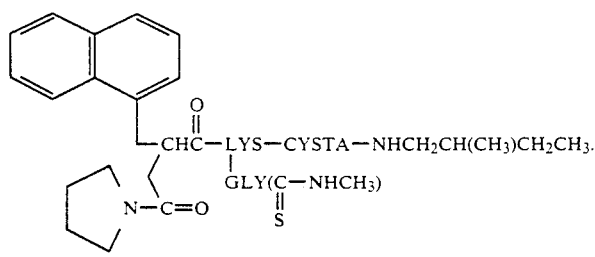
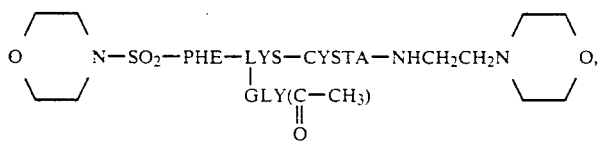
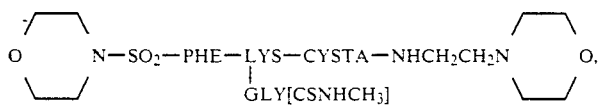
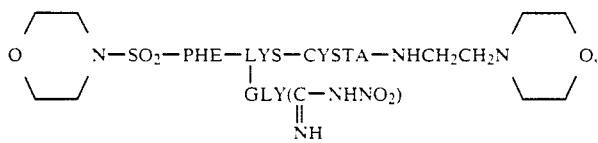
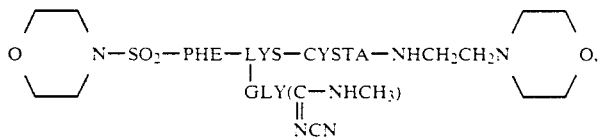
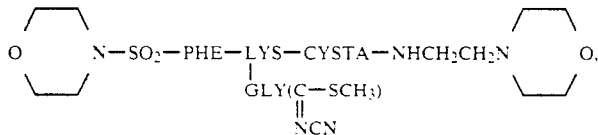
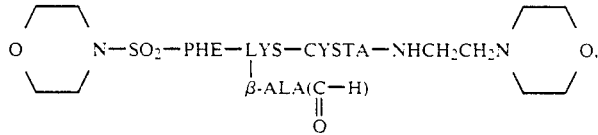
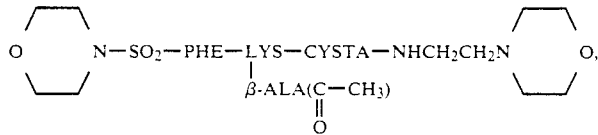
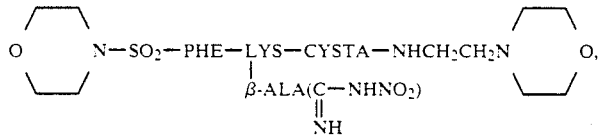
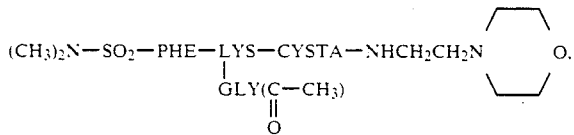

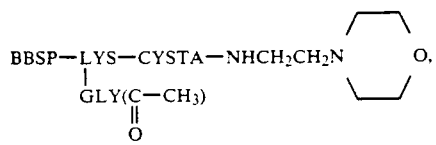
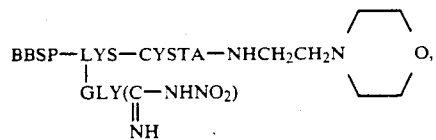
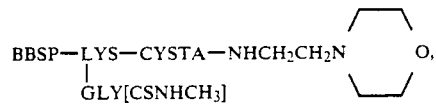
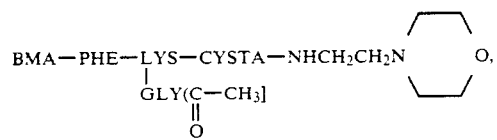
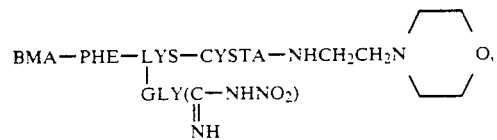
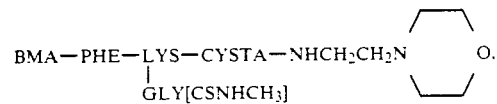
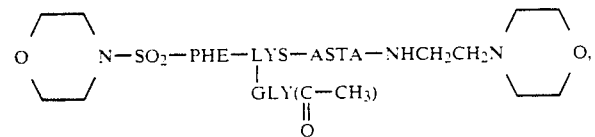
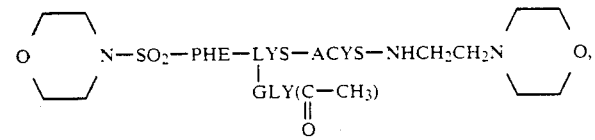
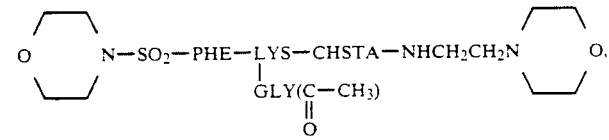
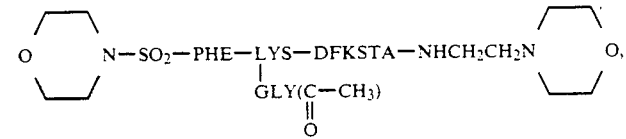
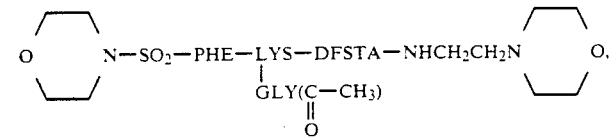

-continued

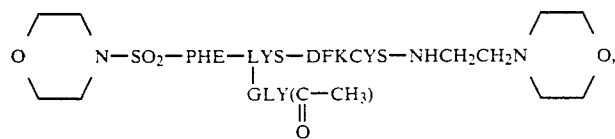

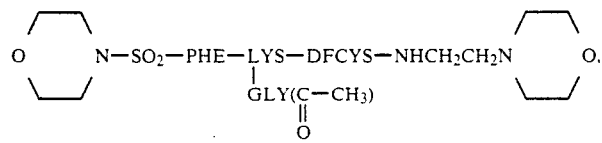

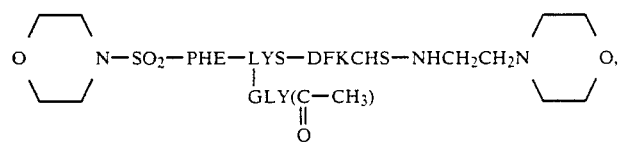

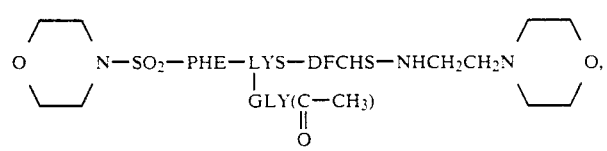

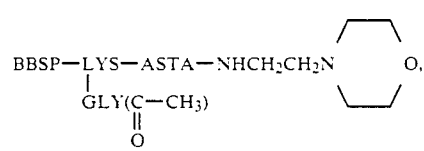

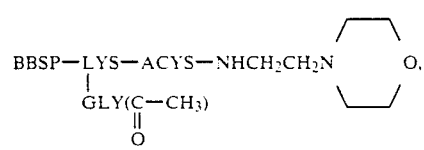

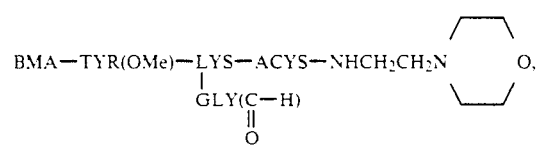

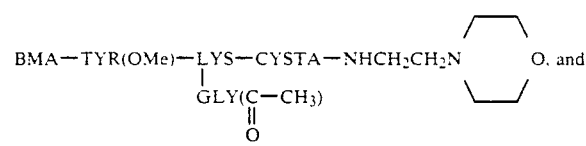

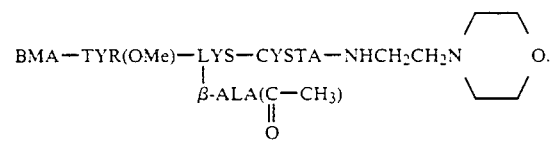

The compounds of the present invention include solvates, hydrates and pharmaceutically acceptable acid addition salts of the basic compounds of formula 1 above.

The term pharmaceutically acceptable acid addition salt is intended to mean a relatively nontoxic acid addition salt either from inorganic or organic acids such as, for example, hydrochloric, hydrobromic, hydroiodic, sulfuric, phosphoric, acetic, citric, oxalic, malonic, salicylic, malic, benzoic, gluconic, fumaric, succinic, ascorbic, maleic, tartaric, methanesulfonic; and the like. The salts are prepared by contacting the free base form with a sufficient amount of the desired acid to produce a salt in the conventional manner. The free base forms may be regenerated by treating the salt form with a base.

The modified peptides of the present invention possess one or more chiral centers and each center may exist in the R(D) or S(L) configuration. The present invention includes all enantiomeric and epimeric forms as well as the appropriate mixtures thereof. Unless otherwise specified, the L form is the preferred embodiment.

Some of the above novel peptides may be prepared in accordance with well-known procedures for preparing peptides from their constituent amino acids. Other of the novel peptides of the present invention are prepared by a step-wise procedure or by a fragment coupling procedure depending upon the particular final product desired.

The strategy of peptide chain assembly and selection and removal of protecting groups is discussed in Chapter 1, "The Peptide Bond," in "The Peptides. Analysis, Synthesis, Biology," E. Gross and J. Meienhofer, Eds., Academic Press, New York, N.Y., 1979, Vol. 1, pp. 42–44.

The DCC/HOBT method of coupling is well-known to those skilled in the art and is discussed in Chapter 5, "The Carbodiimide Method" by D. H. Rich and J. Singh in "The Peptides. Analysis, Synthesis, Biology," E. Gross and J. Meienhofer, Eds., Academic Press, New York, N.Y., 1979, Vol. 1, pp 241–261.

Peptide coupling depends on activating the carboxyl group of the protected amino acid prior to condensing it with another peptide containing a free amino terminus. In addition to the DCC coupling method described above, other methods of activating the carboxyl group of a protected amino acid include:

1) The azide method—described in Chapter 4 of the above reference.
2) The mixed anhydride method—described in Chapter 6 of the above reference.
3) The active ester method—described in Chapter 3 of the above reference.

The acyl groups derived from the substituted succinic acid amides may be prepared as follows. 1-Naphthaldehyde is reacted with diethyl succinate in a Stobbe condensation, and the corresponding di-acid is converted to the anhydride with acetic anhydride. Treatment with the appropriate amine gives 2-(1-naphthylmethylene)-3-(substituted aminocarbonyl) propionic acid. Catalytic hydrogenation gives the desired 2-(1-naphthylmethyl)-3-(substituted aminocarbonyl)propionic acid. This acid may be condensed with suitably protected amino acids using the coupling methods known to peptide chemistry, for example, the carbodiimide method. This is discussed in European Application Publication No. 206,807 and European Application Publication No. 200,406.

The peptide couplings may be performed in a variety of solvents such as DMF, THF, EtOAc, CH$_2$Cl$_2$, CHCHCl$_3$, or CH$_3$CN. The preferred solvents are DMF, THF, and CH$_2$Cl$_2$.

The condensations may be carried out at $-20°$ to $35°$ C. with the preferred temperatures being $-5°$ to $25°$ C.

The reaction time may range from two hours to two days with the preferred time being twelve to twenty-four hours.

The compounds of formula I of the present invention may be prepared in two ways.

In those cases where the side chain of Y terminates with a carboxylic acid function, a peptide of the formula

ACYL—X—Y—W—U—V    IA may be reacted with the amino group of a carboxyl protected amino acid forming the corresponding amide.

In those cases where the side chain of Y terminates with an amino function, a peptide of the formula

ACYL—X—Y—W—U—V    IA may be reacted with the carboxyl portion of an amino protected amino acid forming the corresponding amide.

The compounds of the present invention are useful for treating renin-associated hypertension, congestive heart failure, and peraldosteronism. They are also useful as diagnostic tools for determining the presence of renin-associated hypertension or hyperaldosteronism.

Pharmaceutical compositions which comprise an effective amount of the compound in combination with a pharmaceutically acceptable carrier are part of the present invention. An important aspect of the present invention is a method of treating renin associated hypertension in a mammal which comprises administering a pharmaceutical composition containing an effective amount of a compound of the invention in combination with a pharmaceutically acceptable carrier to the mammal.

Another equally important aspect of the present invention is a method of treating hyperaldosteronism in a mammal which comprises administering a pharmaceutical composition containing an effective amount of a compound of the invention in combination with a pharmaceutically acceptable carrier to the mammal.

Another equally important aspect of the instant invention is a method of treating congestive heart failure in a mammal which comprises administering a pharmaceutical composition containing an effective amount of a compound of the invention in combination with a pharmaceutically acceptable carrier to the mammal.

The effectiveness of the aforementioned compound is determined by a test for in vitro renin inhibitory activity. This activity is determined by a standard radioimmunoassay for angiotensin I. In this assay the enzyme, renin, incubated for two hours at 37° in the presence of a substrate, angiotensinogen, generates the product, angiotensin I. Test compounds are added to the incubation mixture. Relative activity is reported as the IC$_{50}$, which is the molar concentration of test compound causing a 50% inhibition of the renin activity. Relative activity is also reported as % inhibition at $10^{-6}$ M,

| Example | Activity |
|---|---|
| DNMA—GLU—STA—NHCH$_2$CH(CH$_3$)CH$_2$CH$_3$<br>\|<br>GLY[CSNHCH$_3$] | $9.0 \times 10^{-6}$* |
| DNMA—GLU—STA—NHCH$_2$CH(CH$_3$)CH$_2$CH$_3$<br>\|<br>GLY—NHCH$_3$ | $1.5 \times 10^{-5}$* |
| DNMA—ASP—CYSTA—LEU—NHCH$_2$Ph<br>\|<br>MET(O$_2$)—OCH$_3$ | $3.5 \times 10^{-6}$* |
| DNMA—ASP—CYSTA—LEU—NHCH$_2$Ph<br>\|<br>HIS—OCH$_3$ | 32% @ $10^{-6}$** |
| DNMA—ASP—CYSTA—LEU—NHCH$_2$Ph<br>\|<br>GLY[CSNHCH$_3$] | $2.4 \times 10^{-7}$* |
| DNMA—ASP—CYSTA—LEU—NHCH$_2$Ph<br>\|<br>β—ALA—NHCH$_3$ | 47% @ $10^{-6}$** |

-continued

| Example | Activity |
| --- | --- |
| DNMA—ASP—CYSTA—LEU—NHCH$_2$Ph<br>           \|<br>           β—ALA[CSNHCH$_3$] | 49.3% @ $10^{-6}$** |
| DNMA—LYS—STA—NHCH$_2$CH(CH$_3$)CH$_2$CH$_3$<br>           \|<br>           GLY(Z) | 8.3 × $10^{-8}$* |
| DNMA—LYS—STA—NHCH$_2$CH(CH$_3$)CH$_2$CH$_3$<br>           \|<br>           GLY | 7.1 × $10^{-7}$* |
| DNMA—LYS—STA—NHCH$_2$CH(CH$_3$)CH$_2$CH$_3$<br>           \|<br>           GLY(C—NHCH$_3$)<br>                   \|\|<br>                   S | 8.0 × $10^{-8}$* |
| DNMA—LYS—CYSTA—NHCH$_2$CH(CH$_3$)CH$_2$CH$_3$<br>           \|<br>           GLY(C—CH$_3$)<br>                \|\|<br>                O | 2.7 × $10^{-8}$* |
| DNMA—LYS—STA—NHCH$_2$CH(CH$_3$)CH$_2$CH$_3$<br>           \|<br>           TZC(C—CH$_3$)<br>               \|\|<br>               O | 1.1 × $10^{-6}$* |
| DNMA—LYS—STA—NHCH$_2$CH(CH$_3$)CH$_2$CH$_3$<br>           \|<br>           TZC(O$_2$)(C—CH$_3$)<br>                   \|\|<br>                   O | 4.7 × $10^{-7}$* |
| DNMA—LYS—STA—NHCH$_2$CH(CH$_3$)CH$_2$CH$_3$<br>           \|<br>           PGL | 4.3 × $10^{-8}$* |
| DNMA—LYS—STA—NHCH$_2$CH(CH$_3$)CH$_2$CH$_3$<br>           \|<br>           β—ALA(C—CH$_3$)<br>                \|\|<br>                O | 2.5 × $10^{-8}$* |
| DNMA—LYS—STA—NHCH$_2$CH(CH$_3$)CH$_2$CH$_3$<br>           \|<br>           GLY(C—CH(CH$_3$)$_2$)<br>               \|\|<br>               O | 7.4 × $10^{-8}$* |
| DNMA—LYS—STA—NHCH$_2$CH(CH$_3$)CH$_2$CH$_3$<br>           \|<br>           GLY(C—CHF$_2$)<br>               \|\|<br>               O | 6.2 × $10^{-8}$* |
| DNMA—LYS—STA—NHCH$_2$CH(CH$_3$)CH$_2$CH$_3$<br>           \|<br>           GLY(C—NHNO$_2$)<br>               \|\|<br>               NH | 8.0 × $10^{-9}$* |
| DNMA—LYS—STA—NHCH$_2$CH(CH$_3$)CH$_2$CH$_3$<br>           \|<br>           GLY(C—NHCH$_3$)<br>               \|\|<br>               NCN | 3.0 × $10^{-8}$* |

*IC$_{50}$ (M)
**% inhibition at $10^{-6}$ M.

The effectiveness of the aforementioned compounds in vivo is determined by their effect on unanesthetized, sodium-deplete, normotensive Rhesus or Cynomolgus monkeys. Monkeys were acclimated to a low sodium diet and trained to rest quietly in a restraining device. Next vascular access ports were surgically implanted for intravenous administration of test compounds and direct measurement of blood pressure. At least one week was allowed for recovery from surgery before sodium depletion was accomplished by giving furosemide (1 mg/kg/day, IM) for four consecutive days. On the seventh day animals were removed from their home cage and placed in the restraining device. After a twenty to thirty minute acclimation period, a control blood sample (arterial) was taken for determination of PRA. Next, either vehicle (absolute ethanol, 0.2 ml/kg) or test compound (5 mg/kg) was infused intravenously over a ten minute period.

Blood pressure was monitored continuously throughout the entire pre- and post-dose period. Blood samples were taken at the mid-point of the infusion and at 0, 15, 30, and 60 minutes post infusion.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents. It can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

The compounds of the present invention may be administered orally, buccally, parenterally, by inhalation spray, rectally or topically in dosage unit formulations containing conventional nontoxic pharmaceutically acceptable carriers, adjuvants and vehicles as desired. The term parenteral as used herein includes subcutaneous injections, intravenous, intramuscular, intrasternal injection or infusion techniques.

For preparing suppositories, a low melting wax such as a mixture of fatty acid glycerides or cocoa butter is first melted, and the active ingredient is dispersed homgeneously therein by stirring. The molten homogeneous mixture is then poured into convenient sized molds, allowed to cool, and thereby solidify.

Liquid form preparations includes solutions, suspensions, and emulsions. As an example may be mentioned water or water/propylene glycol solutions for parenteral injection. Liquid preparations can also be formulated in solution in aqueous polyethyleneglycol solution. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerin, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be packaged preparation, the package containing discrete quantities of preparation, for example, packeted tablets, capsules, and powders in vials or ampules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient. The compositions can, if desired, also contain other compatible therapeutic agents.

In therapeutic use as renin inhibitors, the mammalian dosage range for a 70 kg subject is from 1 to 1500 mg per day or preferably 25 to 750 mg per day optionally in divided portions. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following Examples are provided to enable one skilled in the art to practice the present invention. These examples are not intended in any way to limit the scope of the invention but are illustrative thereof.

EXAMPLE 1

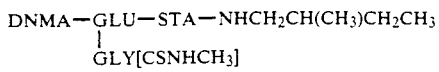

To a solution of 0.98 g (1.41 mmole) of DNMA—GLU—STA—NHCH$_2$CH(CH$_3$)CH$_2$CH$_3$ in 40 ml CH$_2$Cl$_2$ was added a solution of 0.20 g (1.48 mmole) of HOBT in 1 ml DMF. This solution was cooled to 0°, and a solution of 0.30 g (1.62 mmole) of GLY[CSNHCH$_3$].HHr in 10 ml CH$_2$Cl$_2$ was added followed by 0.23 ml (1.65 mmole) of Et$_3$N. 0.31 g (1.48 mmole) of DCC was then added and the mixture stirred and allowed to stand at 3° overnight. The solution was filtered to remove dicyclohexylurea and the DMF was removed under high vacuum. The residue was taken into EtOAc and filtered to remove residual urea. The filtrate was washed with 1 N citric acid, saturated NaCl, saturated NaHCO$_3$, and saturated NaCl. After drying, the solvent was removed under reduced pressure giving a gelatinous solid. The solid was redissolved in warm EtOAc, and precipitated by the addition of Et$_2$O. The solid precipitate was filtered, washed with Et$_2$O and dried under reduced pressure giving a solid, 0.93 g. The structure was confirmed by NMR and mass spectroscopy.

Calcd. for C$_{45}$H$_{59}$N$_5$O$_5$S (MW 782.07): C, 69.11; H, 7.60; N, 8.95; S, 4.10. Found: C, 69.14; H, 7.90; N, 8.84; S, 4.31.

EXAMPLE 2

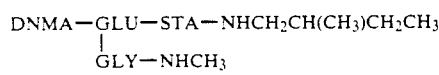

A solution of 0.75 g (1.08 mmole) of DNMA—GLU—STA—NHCH$_2$CH(CH$_3$)CH$_2$CH$_3$ and 0.15 g (1.11 mmole) of HOBT in 30 ml DMF was cooled to 0° and 0.23 g (1.11 mmole) of DCC was added. A cold solution of 0.18 g (2.04 mmole) of GLY—NHCH$_3$ in 5 ml DMF was added, and the mixture was stirred overnight at 4°. The mixture was filtered to remove dicyclohexylurea and the DMF was removed under high vacuum. The residue was taken into EtOAc, filtered, and washed with 1 N citric acid, saturated NaCl, saturated NaHCO$_3$ and saturated NaCl. After drying, the solvent was removed under reduced pressure, leaving the crude product as a brittle foam, 0.97 g. The crude product was chromatographed on silica gel, eluting with CHCl$_3$/MeOH (98,2). Appropriate fractions were combined to give the product, 0.46 g. The structure was confirmed by NMR and mass spectroscopy.

Calcd. for C$_{45}$H$_{59}$N$_5$O$_6$.0.12CHCl$_3$ (MW 780.33): C, 69.45; H, 7.64; N, 8.97; Cl, 1.63. Found: C, 69.11; H, 8.00; N, 8.94; Cl, 1.26.

EXAMPLE 3

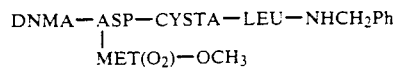

A solution of 250 mg (0.25 mmole) of

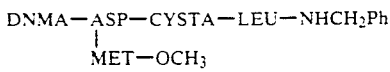

in 10 ml of CH$_2$Cl$_2$ was treated with 155 mg (0.75 mmole) of m-chloroperbenzoic acid and stirred at room temperature overnight. The solvent was removed under reduced pressure and the residue taken up in EtOAc and was led with 10% NaHSO$_3$, H$_2$O, two times with saturated NaHCO$_3$, then with saturated NaCl. Drying and removal of the solvent under reduced pressure left 240 mg of the product as a foam which was transferred to a vial with the aid of CH$_2$Cl$_2$. The structure was confirmed by NMR and mass spectroscopy.

Calcd. for C$_{58}$H$_{73}$N$_5$O$_{10}$S.0.3CH$_2$Cl$_2$ (MW 1057.69): C, 66.20; H, 7.01; N, 6.62. Found: C, 66.12; H, 7.12; N, 6.60.

EXAMPLE 4

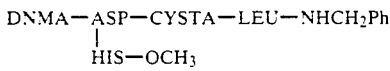

A solution of 700 mg (0.81 mmole) of DNMA—ASP—CYSTA—LEU—NHCH$_2$Ph, 199 mg (0.81 mmole) of HIS—OCH$_3$.2HCl, and 111 mg (0.81 mmole) of HOBT in 20 ml DMF and 10 ml CH$_2$Cl$_2$ was cooled in ice and treated with 0.24 ml (1.62 mmole) of Et$_3$N followed by 171 mg (0.81 mmole) of DCC in 5 ml of DMF. After 0.5 hours at 0°, the mixture was allowed to stir at room temperature for 2 days. The solvent was removed under high vacuum and the residue taken up in EtOAc, filtered, and washed with H$_2$O, saturated NaHCO$_3$, then saturated NaCl. Drying and removal of the solvent under reduced pressure left 810 mg of the crude product. Chromatography on 33 g of silica gel, eluting with CHCl$_3$/MeOH (93/7) gave 410 mg of the pure product as a foam. The structure was confirmed by NMR and mass spectroscopy.

Calcd. for C$_{59}$H$_{71}$N$_7$O$_8$.0.75CHCl$_3$ (MW 1095.75): C, 65.49; H, 6.60; N, 8.95. Found: C, 65.32; H, 6.51; N, 8.84.

EXAMPLE 5

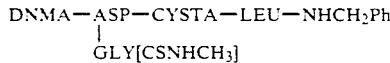

A solution of 600 mg (0.7 mmole) of DNMA—ASP—CYSTA—LEU—NHCH$_2$Ph, 130 mg (0.7 mmole) of glycine, N-methylthioamide.HBr and 95 mg (0.7 mmole) of HOBT in 20 ml of DMF was cooled in ice and treated with 0.1 ml (0.7 mmole) of Et$_3$N followed by 147 mg (0.7 mmole) of DCC in 5 ml of DMF. After 0.5 hours at 0°, the mixture was allowed to stir at room temperature overnight. The solvent was removed under high vacuum and the residue taken up in EtOAc, filtered, and washed with 1 N HCl, H$_2$O, saturated NaHCO$_3$, then saturated NaCl. Drying and removal of the solvent under reduced pressure left 660 mg of the crude product. Chromatography on 27 g silica gel, eluting with CHCl$_3$/MeOH (96/4) gave 300 mg of pure product as a foam. The structure was confirmed by NMR and mass spectroscopy.

Calcd. for C$_{55}$H$_{68}$N$_6$O$_6$.0.5CHCl$_3$ (MW 1000.84): C, 66.60; H, 6.90; N, 8.40. Found: C, 66.72; H, 6.93; N, 8.47.

EXAMPLE 6

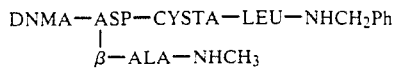

A solution of 700 mg (0.819 mmole) of DNMA—ASP—CYSTA.LEU—NHCH$_2$Ph and 111 mg (0.819 mmole) of HOBT in 20 ml DMF was cooled in ice and treated with 171 mg (0.819 mmole) of DCC in 5 ml of DMF. After stirring at 0° for 1 hour, it was treated with a solution of 114 mg (0.819 mmole) β-ALA—NHCH$_3$.HCl in 5 ml DMF, followed by 0.12 ml (0.819 mmole) of Et$_3$N. The cooling was removed and the mixture allowed to stir at room temperature overnight. The solvent was removed under high vacuum and the residue taken up in EtOAc, filtered, and washed in 1 N HCl, H$_2$O, saturated NaHCO$_3$, then saturated NaCl. Drying and removal of the solvent under reduced pressure left the crude product. Chromatography on 36 g of silica gel, eluting with CHCl$_3$/MeOH (95/5) gave 217 mg of pure product, mp 208°–210°. The structure was confirmed by NMR and mass spectroscopy.

Calcd. for C$_{56}$H$_{70}$N$_6$O$_7$ (MW 939.17): C, 71.61; H, 7.51; N, 8.95. Found: C, 71.62; H, 7.59; N, 8.97.

EXAMPLE 7

A solution of 600 mg (0.7 mmole) of DNMA—ASP—CYST—LEU—NHCH$_2$Ph, 140 mg (0.7 mmole) of β-ALA[CSNHCH$_3$].HBr, and 98 mg (0.7 mmole) of HOBT in 15 ml DMF was cooled in ice and treated with 0.1 ml (0.7 mmole) of Et$_3$N followed by 147 mg (0.7 mmole) of DCC in 5 ml of DMF. After 0.5 hour at 0°, the mixture was allowed to stir at room temperature overnight. The solvent was removed under high vacuum and the residue taken up in EtOAc, filtered and the filtrate washed with 1 N HCl, H$_2$O, saturated NaHCO$_3$, then saturated NaCl. Drying and removal of the solvent under reduced pressure left the crude product. Chromatography on 27 g of silica gel, eluting with CHCl$_3$/MeOH (97/3) gave 290 mg of pure product as a foam. The structure was confirmed by NMR and mass spectroscopy.

Calcd. for C$_{56}$H$_{70}$N$_6$O$_6$S.0.6CHCl$_3$ (MW 1026.80): C, 66.20; H, 6.93; N, 8.19. Found: C, 66.45; H, 6.92; N, 7.90.

EXAMPLE 8

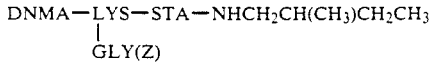

A solution of 500 mg (0.72 mmole) of DNMA—LYS—STA—NHCH$_2$CH(CH$_3$)CH$_3$, 150 mg (0.72 mmole) of Z—GLY, and 100 mg (0.74 mmole) of HOBT in 10 ml of DMF was cooled in ice and treated with 150 mg (0.72 mmole) of DCC in 5 ml of DMF. After 0.5 hour at 0°, the mixture was allowed to stir at room temperature overnight. The urea was filtered off and the filtrate diluted with EtOAc, washed with H$_2$O, saturated NaHCO$_3$, then saturated NaCl. Drying and removal of the solvent under reduced pressure left the crude product. Chromatography on silica gel, eluting with EtOAc/- hexane (1/1) then with EtOAc/MeOH (10/1) gave 600 mg of product. The structure was confirmed by IR, NMR, and mass spectroscopy.

Calcd. for $C_{53}H_{67}N_5O_7$ (MW 866.11): C, 71.83; H, 7.62; N, 7.90. Found: C, 71.49; H, 7.65; N, 7.95.

EXAMPLE 9

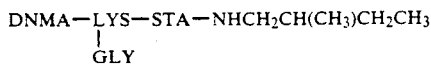

A solution of 400 mg (0.46 mmole) of

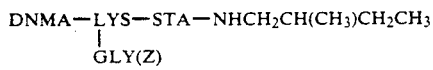

in 15 ml of MeOH was treated with 50 mg of 20% Pd/C and stirred under an atmosphere of hydrogen for 2 hours. The mixture was filtered and the solvent removed under reduced pressure. The residue was transferred to a vial with the aid of $CHCl_3$ to give 300 mg of product. The structure was confirmed by IR, NMR, and mass spectroscopy.

Calcd. for $C_{45}H_{61}N_5O_5 \cdot 0.2CHCl_3$ (MW 775.91): C, 69.97; H, 7.95; N 9.03. Found: C, 69.83; H, 8.13; N, 9.11.

EXAMPLE 10

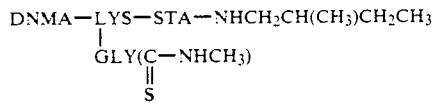

A solution of 438 mg (0.56 mmole) of

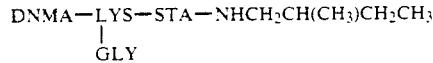

in 10 ml $CHCl_3$ was cooled to 0° and treated with 40 mg (0.56 mmole) of methyl isothiocyanate. The cooling was removed and the solution allowed to stir at room temperature overnight. The solvent was removed under reduced pressure and the residue chromatographsd on silica gel, eluting with EtOAc/MeOH (9/1). There was obtained 320 mg of the product as a foam. The structure was confirmed by IR, NMR, and mass spectroscopy.

Calcd. for $C_{47}H_{64}N_6O_5S \cdot 0.8CH_3OH$ (MW 850.66): C, 67.49; H, 7.96; N, 9.88. Found: C, 67.44; H, 8.20; N, 9.52.

EXAMPLE 11

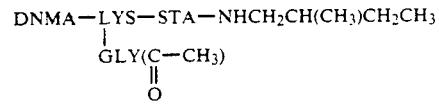

A solution of 500 mg (0.72 mmole) of DNMA—LYS—STA—$NHCH_2CH(CH_3)CH_2CH_3$, 85 mg (0.72 mmole) of N-acetylglycine, and 100 mg (0.72 mmole) of HOBT in 10 ml DMF is cooled in ice and treated with 150 mg (0.72 mmole) of DCC in 5 ml of DMF. After 0.5 hour at 0°, the mixture is allowed to stir at room temperature overnight. The urea is filtered off and the solvent removed under reduced pressure. The residue is taken up in EtOAc, filtered, and the filtrate washed with 1 N HCl, $H_2O$, saturated $NaHCO_3$, then saturated NaCl. Drying and removal of the solvent under reduced pressure leaves the crude product which can be purified by chromatography on silica gel, eluting with $CHCl_3$/MeOH (95/5).

EXAMPLE 12

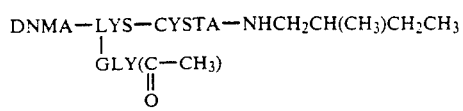

A solution of 168 mg (1.4 mmole) of N-acetylglycine and mg (1.4 mmole) of HOBT in 10 ml of DMF was cooled in ice and 298 mg (1.4 mmole) of DCC added, followed by 1.05 g (1.4 mmole) of DNMA—LYS—CYSTA—$NHCH_2CH(CH_3)CH_2CH_3$ in 10 ml DMF. After 0.5 hour at 0°, the mixture was allowed to stir at room temperature overnight. The mixture was filtered and the DMF removed under high vacuum. The residue was taken up in EtOAc, filtered, and washed with 1 N HCl, water, saturated $NaHCO_3$, then saturated NaCl. Drying and removal of the solvent under reduced pressure left the crude product. This was taken up in EtOAc with a little MeOH, and poured into excess hexane. The solid was collected and washed with hexane to give 860 mg of product. The structure was confirmed by NMR and mass spectroscopy.

Calcd. for $C_{50}H_{67}N_5O_6 \cdot 0.2H_2O$ (MW 837.68): C, 71.69; H, 8.11; N, 8.36. Found: C, 71.51; H, 8.38; N, 8.11.

EXAMPLE 13

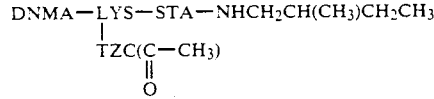

A solution of 253 mg (1.44 mmole) of N-acetyl-4-thiazolidinecarboxylic acid, 220 mg (1.58 mmole) of HOBT, and 1.0 g (1.44 mmole) of DNMA—LYS—STA—$NHCH_2CH(CH_3)CH_2CH_3$ in 10 ml of DMF was cooled in ice and treated with a solution of 326 mg (1.58 mmole) of DCC in 5 ml of DMF. After 0.5 hour at 0°, the mixture was allowed to stir at room temperature for 48 hours. The mixture was filtered and the filtrate evaporated under high vacuum. The residue was taken up in EtOAc and washed with $H_2O$, saturated $NaHCO_3$, and then brine. Drying and removal of the solvent under reduced pressure gave the crude product. This was purified by chromatography on silica gel, eluting with $CH_2Cl_2$/MeOH (95/5), and giving 0.7 g of the product. The structure was confirmed by NMR and mass spectroscopy.

Calcd. for $C_{49}H_{65}N_5O_6S \cdot 0.55\ CHCl_3$ (MW 917.82): C, 64.86; H, 7.20; N, 7.63; Cl, 6.38. Found: C, 64.32; H, 7.06, N, 7.12; Cl, 6.35.

EXAMPLE 14

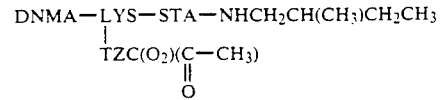

A solution of 120 mg (0.59 mmole) of m-chloropenbenzoic acid in 5 ml of $CHCl_3$ was added dropwise to a cold solution of 0.5 g (0.59 mmole) of the product from Example 13 in 10 ml of CHCl₃. After stirring at room temperature overnight the mixture was washed with saturated NaHCO₃, then brine. After drying and removal of the solvent under reduced pressure, there was obtained 0.6 g of a mixture of the sulfone and sulfoxide. Chromatography on silica gel, eluting with CHCl₃/MeOH (97.5/2.5) gave 0.1 g of the product. The structure was confirmed by NMR and mass spectroscopy.

Calcd. for C₄₉H₆₅N₅O₈S.0.06 CHCl₃ (MW 891.32): C, 65.96; H, 7.30; N, 7.85. Found: C, 66.00; H, 7.55; N, 7.58.

EXAMPLE 15

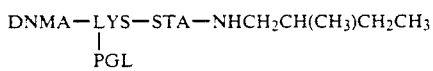

A solution of 260 mg (2.0 mmole) of L-pyroglutamic acid, mg (2.0 mmole) of HOBT, and 1.5 g (2.0 mmole) of DNMA—LYS—STA—NHCH₂CH(CH₃)CH₂CH₃ in 25 ml of CH₂Cl₂ was cooled in ice and treated with a solution of 420 mg (2.0 mmole) of DCC in 10 ml CH₂Cl₂. After 0.5 hour at 0°, the mixture was allowed to stir at room temperature for 2 days. The mixture was filtered, and the filtrate washed with H₂O, saturated NaHCO₃, and brine. Drying and removal of the solvent under reduced pressure gave the crude product which was purified by chromatography on silica gel, eluting with CH₂Cl₂/MeOH (95/5). There was obtained 0.8 g of product. The structure was confirmed by NMR and mass spectroscopy.

Calcd. for C₄₈H₆₃N₅O₆.0.6 H₂O (MW 816.88): C, 70.60; H, 7.87; N, 8.58. Found: C, 70.38; H, 8.12; N, 8.13.

EXAMPLE 16

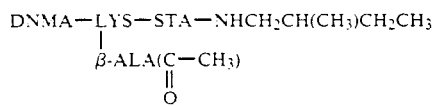

A solution of 1.49 g (1.83 mmole) of Et₃N

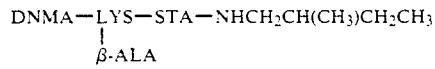

in a mixture of 50 ml THF and 200 ml of CH₃CN was treated with 200 mg (1.83 mmole) of Et₃N followed by 150 mg (1.83 mmole) of acetyl chloride. The mixture was stirred at room temperature overnight, and an additional 150 mg of acetyl chloride was added. The solvent was then removed under reduced pressure and the crude product chromatographed on silica gel, eluting with CHCl₃/MeOH (96/4). There was obtained 0.67 g of an oil. NMR showed this to be the O,N-diacetate.

This material was dissolved in 20 ml of MeOH/H₂O 1:1) and 5.5 g (40 nmole) of K₂CO₃ added and the solution stirred at room temperature overnight. The solvent was removed under reduced pressure and the residue taken up in EtOAc and washed with H₂O. Drying and removal of the solvent under reduced pressure gave a foam which was chromatographed on silica gel, eluting with CHCl₃/MeOH (97/3). There was obtained 0.5 g of product. The structure was confirmed by NMR and mass spectroscopy.

Calcd. for C₄₈H₆₅N₅O₆ (MW 808.04): C, 71.34; H, 8.11; N, 8.67. Found: C, 71.71; H, 8.27; N, 8.14.

EXAMPLE 17

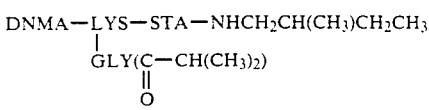

A solution of 140 mg (1.33 mmole) of isobutyryl chloride in 5 ml CH₂Cl₂ was added to a cold solution of 1.0 g (1.33 mmole) of

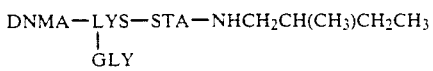

in 15 ml CH₂Cl₂ containing 130 mg (1.33 mmole) of Et₃N. After 0.5 hour at 0°, the solution was allowed to stir at room temperature for 24 hours. The solution was then washed with H₂O, dried, and stripped to give 1.0 g of the crude product. Chromatography on silica gel, eluting with CH (95/5) gave 0.6 g of the product. The structure was confirmed by NMR and mass spectroscopy.

Calcd. for C₄₉H₆₇N₅O₆.0.6 H₂O (MW 832.97): C, 70.69; H, 8.20; N, 8.42. Found: C, 70.34; H, 8.56; N, 8.48.

EXAMPLE 18

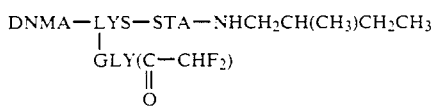

A solution of 130 mg (1.33 mmole) of difluoroacetic acid, 110 mg (1.33 mmole) of HOBT, and 1.0 g (1.33 mmole) of

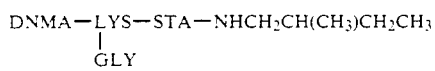

in 15 ml CH₂Cl₂ was cooled in ice and treated with 280 mg (1.33 mmole) of DCC in 10 ml CH₂Cl₂. After 0.5 hour at 0°, the mixture was allowed to stir at room temperature for 48 hours. The mixture was then filtered and the filtrate washed with H₂O, saturated NaHCO₃, and brine. Drying and removal of the solvent under reduced pressure gave the crude product. Chromatography on silica gel, eluting with CH₂Cl₂/MeOH (95/5) gave 0.4 g of product. The structure was confirmed by NMR and mass spectroscopy.

Calcd. for C₄₇H₆₁N₅O₆F₂.0.7 H₂O (MW 842.65): C, 67.01; H, 7.41; N, 8.32. Found: C, 66.70; H, 7.76; N, 8.55.

EXAMPLE 19

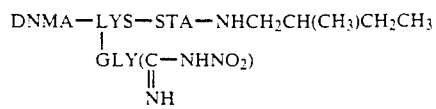

A solution of 260 mg (1.88 mmole) of 2-methyl-1-nitro-2-thiopseudourea in 35 ml CH₃CN was added dropwise to a solution of 1.41 g (1.88 mmole) of

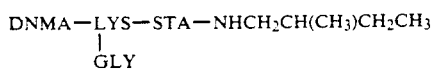

in 30 ml of CHCl₃ and the mixture allowed to stir at room temperature overnight. The solvent was removed under reduced pressure and the residue chromatographed on silica gel, eluting with CHCl₃/MeOH (95/5). There was obtained 0.51 g of product. The structure was confirmed by NMR and mass spectroscopy.

Calcd. for $C_{47}H_{62}N_8O_7 \cdot 0.19$ CHCl₃·0.05 CH₂Cl₂ (MW 877.96): C, 64.62; H, 7.15; N, 12.76. Found: C, 64.08; H, 7.38; N, 12.93.

EXAMPLE 20

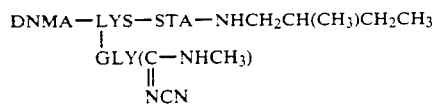

Methylamine gas was passed into a solution of 1.66 g (1.85 mmole) of

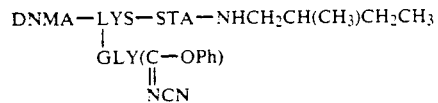

in 70 ml CH₂Cl₂ until saturation, and the solution was stirred for 24 hours. The solvent was removed under reduced pressure and the residue chromatographed on silica gel, eluting with CHCl₃/MeOH (97/3), and yielding 0.96 g of product. The structure was confirmed by NMR and mass spectroscopy.

Calcd. for $C_{48}H_{64}N_8O_5 \cdot 0.13$ CHCl₃ (MW 848.62): C, 68.13; H, 7.62; N, 13.21. Found: C, 68.04; H, 7.66; N, 13.27.

INTERMEDIATES FOR EXAMPLES 1 AND 2

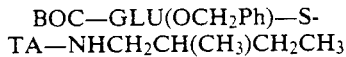

A solution of 6.72 g (14.6 mmole) of BOC—GLU(OCH₂Ph)-p-nitrophenyl ester in 75 ml DMF was cooled to −5°. 4.12 g (14.6 mmole) STA—NHCH₂CH(CH₃)CH₂CH₃·HCl was dissolved in 50 ml cold DMF to which was added 2.08 ml (15 mmole) of Et₃N. The two solutions were combined and allowed to warm to 25° with stirring over 3 hours, followed by storage at 4° for 2 days. The mixture was filtered to remove Et₃N·HCl and the filtrate was evaporated under high vacuum. The residue was taken up in EtOAc and washed with 1 N citric acid, saturated NaCl, saturated NaHCO₃, and saturated NaCl. Drying and removal of the solvent under reduced pressure left 8.2 g of an oil. Crystallization of the oil from EtOAc/hexane gave a white solid, 7.53 g, of sufficient purity to use in the subsequent reactions. The structure was confirmed by mass spectroscopy.

To a solution of 6.83 g (12.1 mmole) of BOC—GLU(OCH₂Ph)—STA—NHCH₂CH(CH₃)CH₂CH₃ in 75 ml CH₂Cl₂ was added 20 ml TFA. After stirring for 2 hours at room temperature, the mixture was evaporated in vacuo to an oil, dissolved in CH₂Cl₂ and again evaporated to an oil. The residue was taken into EtOAc and washed with saturated NaCl which had been treated with sufficient 5 N NaOH to maintain a pH of 10. The organic phase was washed with saturated NaCl, dried, and evaporated under reduced pressure, giving the crude product as a green syrup, 6.07 g. The crude product was chromatographed on silica gel, eluting with CHCl₃/MeOH (95/5). Combining the appropriate fractions gave 3.98 g of an oil, suitable for use in the following reactions.

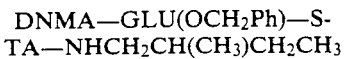

A solution of 2.86 g (8.41 mmole) of di-(1-naphthylmethyl)acetic acid, 3.90 g (8.41 mmole) of GLU-(OCH₂Ph)—STA—NHCH₂CH(CH₃)CH₂CH₃, and 1.19 g (8.83 mmole) HOBT in 170 m]DMF was cooled to 5°. 1.82 g (8.83 mmole) DCC was added, and the mixture was kept at 4° for 4 days. Dicyclohexylurea was removed by filtration, and the DMF was removed under high vacuum. The residue was taken up in EtOAc and washed with 1 N citric acid, saturated NaCl, saturated NaHCO₃ and saturated NaCl. Drying and removal of solvent under reduced pressure left the crude product as a brittle foam, 6.29 g. The crude product was chromatographed on silica gel, eluting with a gradient of 0 to 5% MeOH in CHCl₃. Combining the appropriate fractions gave the product as a brittle foam, 4.80 g, suitable for use in the following reactions. The structure was confirmed by mass spectroscopy.

To a solution of 4.77 g (6.07 mmole) of DNMA—GLU(OCH₂Ph)—STA—NHCH₂CH(CH₃)CH₂CH₃ in 150 ml MeOH was added 0.4 g of 20% palladium on charcoal catalyst. After purging the solution with hydrogen for 6 hours, the suspension was filtered and the solvent removed under reduced pressure. The residue was chromatographed on silica gel eluting with a gradient of 0 to 5% MeOH in CHCl₃. The appropriate fractions were combined, giving the product as a brittle foam, 2.09 g, of sufficient purity for use in subsequent reactions. The structure was confirmed by mass spectroscopy.

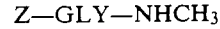

To a solution of 31.38 g (150 mmole) of Z—GLY in 300 ml CH₂Cl₂ was added 18.6 ml (150 mmole) of m-methylpiperidine. After stirring 20 minutes at −5°, 19.5 ml (150 mmole) of isobutyl chloroformate was added over 15 minutes. After stirring an additional 1.5 minutes, 15 g (480 mmole) N-methylamine was added, with exotherm to 20°. After cooling at 0° for 2 hours, the solvent was removed under reduced pressure, and the residue was suspended in EtOAc. The suspension was washed with 1 N citric acid, saturated NaCl, saturated NaHCO₃, and saturated NaCl. After drying, the volume of the solution was reduced under reduced pressure, giving a crystalline solid. The suspension was diluted with Et₂O, filtered, and dried, giving 19.8 g of the product as a crystalline solid. The product was of sufficient purity for use in the subsequent reactions. The structure was confirmed by NMR, IR, and elemental analysis.

GLY—NHCH₃

To a solution of 7.0 g (31.5 mmole) of Z—GLY—NHCH in 125 ml MeOH was added 0.5 g of 20% palladium on carbon catalyst. The suspension was purged with hydrogen for 3 hours, and an additional 0.2 g of catalyst was added. After an additional 1.5 hours, the suspension was filtered and the solvent removed under reduced pressure giving the product as an oil, 3.02 g, which was of sufficient purity for use in subsequent reactions. The structure was confirmed by mass spectroscopy.

Z—GLY[CSNHCH₃]

A suspension of 3.89 g (17.5 mmole) of Z—GLY—NHCH₃ and 3.89 g (17.5 mmole) of $P_2S_5$ in 40 ml toluene was heated to 75° for 45 minutes, and the supernatant liquid decanted from the solid residue. The solid residue was triturated with toluene and the decantates were combined, and washed with 1 N citric acid. The organic phase was diluted with EtOAc and washed with saturated NaCl, saturated NaHCO₃, and saturated NaCl. Drying and removal of solvent under reduced pressure gave 2.32 g of the crude product as a yellow solid. The product was recrystallized from EtOAc/Et₂O giving a white solid, 1.54 g, of sufficient purity for use in subsequent reactions.

GLY[CSNHCH₃].HBr

A solution of 1.55 g (6.5 mmole) of Z—GLY[CSNHCH₃] in 10 ml of 31% HBr in HOAc was stirred at room temperature for 80 minutes. The solvent was removed under reduced pressure with brief warming. The solid residue was triturated with Et₂O, filtered and washed with Et₂O, giving 1.18 g of a yellow solid, of sufficient purity for use in subsequent reactions. The structure was confirmed by mass spectroscopy.

BOC—STA—NHCH₂CH(CH CH₂CH₃

BOC—STA (27.53 g, 0.1 mole, U.S. Pat. No.4,397,786) and HOBT (14.2 g, 0.105 mole) were dissolved in 40 ml DMF. 300 ml CH₂Cl₂ was added, and the mixture was cooled to 0°. A solution of DCC (21.66 g, 0.105 mole) in 50 ml CH₂Cl₂ was added, followed by S-2-methylbutylamine (12 ml, 0.1 mole). After stirring at 0° for two hours, the mixture was allowed to warm to 25° over 1.5 hours. The mixture was filtered, and the solvent was removed in vacuo. The residue was dissolved in EtOAc, which was washed with 1 N citric acid, brine, saturated NaHCO₃ solution, and brine. The organic phase was dried over MgSO₄, filtered, and stripped to a gum, 36.90 g. The gum was dissolved in Et₂O and treated with charcoal to remove colored impurities. The suspension was filtered and stripped to a gum, 35.2 g, which was suitable for use in the following procedure without further purification.

STA—NHCH₂CH(CH₃)CH₂CH₃.HCl

BOC—STA—NHCH₂CH(CH₃)CH₂CH₃ (34.4 g, 0.1 mole) was dissolved in 250 ml CH₂Cl₂, and the solution was purged occasionally with anhydrous HCl gas over three hours. A solid precipitated from solution which was filtered, washed with CH₂Cl₂, and dried at 40° in vacuo to a hygroscopic solid, 21 g. The solid was triturated with a mixture of CH₂Cl₂/Et₂O, filtered, and dried at 40° in vacuo to a white solid, 19.34 g. Spectral analysis confirmed the structure.

INTERMEDIATES FOR EXAMPLES 3-7

BOC—CYSTA—LEU—NHCH₂Ph

A solution of 8.0 g (25.4 mmole) of BOC—CYSTA, 6.7 g (25.4 mmole) of LEU—NHCH₂Ph.HCl [Japan 83/59952], and 3.43 g (25.4 mmole) <,f HOBT in 100 ml DMF was cooled in ice and treated with 3.6 ml (25.4 mmole) of Et₃N followed by 5.29 g (25.4 mmole) of DCC in 10 ml of DMF. After stirring at 0° for 0.5 hour, the mixture was allowed to stir at room temperature overnight.

The urea was filtered off and the solvent removed under high vacuum at 40°. The residue was taken up in EtOAc, filtered, and washed with 1 N HCl, H₂O, saturated NaHCO₃, then saturated NaCl. After removal of the solvent under reduced pressure, the residue was chromatographed on 520 g of silica gel, eluting with CHCl₃/MeOH (98/2). Combining the appropriate fractions gave 13.1 g of product, suitable for use in the following reaction. The structure was confirmed by mass spectroscopy.

CYSTA—LEU—NHCH₂Ph.HCl

A solution of 13.1 g (25.3 mmole) of BOC—CYSTA—LEU—NHCH₂Ph in 100 ml of CH₂Cl₂ was treated with HCl gas for 1 hour. The solvent was removed under reduced pressure, the residue taken up in CH₂Cl₂ and the solvent again removed under reduced pressure leaving 8.2 g of a foam. Mass spectra confirmed the structure.

Calcd. for $C_{24}H_{39}N_3O_3.HCl.0.2H_2O$ (MW 457.64): C, 62.98; H, 8.90; N, 9.18. Found: C, 62.92; H, 8.83; N, 9.14.

BOC—ASP(OCH₂Ph)—CYSTA—LEU—NHCH₂Ph

A solution of 5.0 g (10.9 mmole) of CYSTA—LEU—NHCH₂Ph.HCl, 3.54 g (10.9 mmole) of BOC-β-benzylaspartic acid, and 1.48 g (10.9 mmole) of HOBT in 50 ml of DMF was cooled in ice and treated with 1.53 ml (10.9 mmole) of Et₃N followed by 2.28 g (10.9 mmole) of DCC in 10 ml DMF. After stirring for 1 hour at 0°, the mixture was allowed to stir at room temperature overnight.

The urea was filtered off and the DMF removed under high vacuum. The residue was taken up in EtOAc, filtered, and washed with 1 N HCl, H₂O, saturated NaHCO₃, then saturated NaCl. Drying and removal of the solvent under reduced pressure left 7.8 g of the product of sufficient purity to use in subsequent reactions. The structure was confirmed by mass spectroscopy.

ASP(OCH₂Ph)—CYSTA—LEU—NHCH₂Ph

A solution of 7.8 g (10.8 mmole) of BOC—ASP(OCH₂Ph)—CYSTA—LEU—NHCH₂Ph in 75 ml of CH₂Cl₂ was treated with 50 ml of TFA and stirred at room temperature for 1 hour. The solvent was removed under reduced pressure, CH₂Cl₂ added, and the solvent removed again under reduced pressure. The residue was taken up in EtOAc, washed twice with saturated NaHCO₃, then with saturated NaCl. Drying and removal of the solvent under reduced pressure left 6.7 g of the product as a foam. The structure was confirmed by mass spectroscopy.

DNMA—ASP(OCH₂Ph)—CYS-TA—LEU—NHCH₂Ph

A solution of 3.69 g (10.8 mmole) of di-(1-naphthylmethyl)acetic acid, 6.74 g (10.8 mmole) of ASP-(OCH₂Ph)—CYSTA—LEU—NHCH₂Ph, and 1.47 g (10.8 mmole) of HOBT in 70 ml DMF was cooled in ice and treated with 2.26 g (10.8 mmole) of DCC in 10 ml DMF. After 0.5 hour at 0°, the mixture was left stirring at room temperature overnight. The urea was filtered off and the solvent removed under high vacuum. The residue was taken up in EtOAc, filtered, washed with 1 N HCl, H₂O, saturated NaHCO₃, then saturated NaCl. Drying and removal of the solvent under reduced pressure left the crude product. Chromatography on 350 g of silica gel, eluting with CHCl₃/MeOH (98/2) gave 9.38 g of product. The structure was confirmed by NMR and mass spectroscopy.

Calcd. for C₅₉H₆₈N₄O₇.0.6CHCl₃ (MW 1016.80): C, 70.40; H, 6.80; N, 5.51. Found: C, 70.59; H, 6.93; N, 5.58.

DNMA—ASP—CYSTA—LEU—NHCH₂Ph

A solution of 9.1 g (9.6 mmole) of DNMA—ASP-(OCH₂Ph)—CYSTA—LEU—NHCH₂Ph in 230 ml of MeOH was treated with 1.0 g of 20% Pd/C and stirred under a hydrogen atmosphere for 6 hours. The mixture was filtered and the solvent removed under reduced pressure leaving 7.29 g of the product as a foam. The structure was confirmed by mass spectroscopy.

INTERMEDIATES FOR EXAMPLE 3

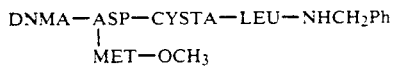

A solution of 1.0 g (1.2 mmole) of DNMA—ASP—CYSTA—LEU—NHCH₂Ph, 234 mg (1.2 mmole) of MET—OCH₃.HCl, and 158 mg (1.2 mmole) of HOBT in 20 ml of DMF was cooled in ice and treated with 1.7 ml (1.2 mmole) of Et₃N followed by 250 mg (1.2 mmole) of DCC in 5 ml of DMF. After 0.5 hour at 0°, the mixture was allowed to stir at room temperature overnight. The urea was filtered off and the residue taken up in EtOAc, filtered, and washed with 1 N HCl, H₂O, saturated NaHCO₃, then saturated NaCl. Drying and removal of the solvent under reduced pressure left the crude product as a foam. Chromatography on silica gel, eluting with CHCl₃/MeOH (98/2) gave 640 mg of the pure product as a foam. The structure was confirmed by NMR and mass spectroscopy.

Calcd. for C₅₈H₇₃N₅O₈S.0.2CHCl₃ (MW 1024.08): C, 68.25; H, 7.21; N, 6.84. Found: C, 68.22; H, 7.36; N, 7.23.

INTERMEDIATES FOR EXAMPLE 6

Z—β-ALA—NHCH

A solution of 15.0 g (67.2 mmole) of Z-β-ALA (J. Biol. Chem., 108, 753 (1935).) in 150 ml CH₂Cl₂ and 50 ml THF was treated with 9.38 ml (67.2 mmole) of Et₃N and cooled in an ice-salt bath. To this was added dropwise rapidly 5.2 ml (67.2 mmole) cf methylchloroformate. After stirring for 5 minutes the solution was treated dropwise with a solution of 10 ml of condensed methylamine in 100 ml CH₂Cl₂ and cooled to −50°. After the addition was complete, the mixture was kept at 0° for 0.5 hour, then allowed to warm to room temperature over 2 hours. The solvent was removed under reduced pressure and the residue mixed with H₂O and extracted twice with CHCl₃. The CHCl₃ was washed with 1 N HCl, H₂O, saturated NaHCO₃, then saturated NaCl. After drying and removal of the solvent under reduced pressure, the residue was recrystallized from EtOAc/hexane to give 11.5 g of product, mp 130°-131°. The structure was confirmed by NMR spectroscopy.

Calcd. for C₁₂H₁₆N₂O₃ (MW 236.26): C, 61.00; H, 6.83; N, 11.86. Found: C, 60.76; H, 6.71; N, 11.77.

β-ALA—NHCH₃.HCl

A solution of 2.0 g (8.5 mmole) of Z-β-ALA—NHCH₃ in 25 ml MeOH was treated with 0.2 g of 20% Pd/C and stirred under a hydrogen atmosphere for 4 hours. The mixture was filtered and the solvent removed under reduced pressure leaving a white solid. This was suspended in CHCl₃ and HCl as bubbled through the mixture. Et₂O was added and the mixture stripped to a gum. Trituration with Et₂O gave 1.0 g of the product as a white solid.

INTERMEDIATES FOR EXAMPLE 7

Z-β-ALA[CSNHCH₃]

Under argon, a suspension of 5.0 g (21.2 mmole) of Z-β-ALA—NHCH₃ in 50 ml of toluene was treated with 6.0 g (14.8 mmole) of Lawesson's reagent and heated at 97° for 4 hours. Solution occurred after 20 minutes. The solution was diluted with EtOAc and washed with 1 N HCl, H₂O, saturated NaHCO₃, and then saturated NaCl. Drying and removal of the solvent under reduced pressure left the crude product as an oil. Chromatography on 213 g of silica gel, eluting with CHCl₃/MeOH (99/1) gave the product. Recrystallization from CHCl₃/hexane gave 4.0 g of the product as white solid, mp 70°-71°. The structure was confirmed by NMR and mass spectroscopy.

Calcd. for C₁₂H₁₆N₂O₂S (MW 252.26): C, 57.13; H, 6.39; N, 11.11. Found: C, 57.18; H, 6.51; N, 11.21.

β-ALA[CSNHCH₃].HBr

A suspension of 2.0 g (7.9 mmole) of Z-β-ALA[CSNHCH ] in 30 ml of 31% HBr in HOAc was stirred at room temperature for 2 hours. The solvent was removed under reduced pressure and the residue taken up in H₂O and washed three times with CHCl₃ and twice with Et₂O. The aqueous phase was freeze-dried to give 1.36 g of the product as a tan solid. The structure was confirmed by NMR spectroscopy.

INTERMEDIATES FOR EXAMPLES 8-11, 13, 15

BOC—LYS(Z)—STA—NHCH₂CH(CH₃)CH₂CH₃

BOC—LYS(Z) (1.98 g), STA—NHCH₂CH(CH₃)CH₂CH₃.HCl (1.5 g), hydroxybenzotriazole (0.72 g), and triethyl amine (0.74 ml) were mixed together in DMF (15 ml) and cooled to 0°. Dicyclohexylcarbodiimide (1.1 g) was added, and the mixture was allowed to warm slowly to 25° and then stir for 72 hours. The mixture was filtered, and the filtrate was diluted with EtOAc and extracted with water. The organic phase was washed with water, sodium bicarbonate solution, and brine. The organic phase was dried over sodium sulfate, filtered, and evaporated. The residue was eluted from silica gel with 1:1 EtOAc/hexane to give 2.7 g of product.

LYS(Z)—STA—NHCH₂CH(CH₃)CH₂CH₃

BOC—LYS(Z)—STA—NHCH₂CH(CH₃)CH₂CH₃ (2.7 g) was dissolved in dichloromethane (30 ml), and trifluoroacetic acid (4 ml) was added. The mixture was stirred for 2 hours at 25°. The solvent was evaporated, and the residue was extracted with EtOAc and sodium carbonate solution. The organic phase was washed with brine, dried over sodium sulfate, filtered, and evaporated to give 2.1 g of the product.

DNMA—LYS(Z)—STA—NHCH$_2$CH(CH$_3$)CH$_2$CH$_3$

LYS(Z)—STA—NHCH$_2$CH(CH$_3$)CH$_2$CH$_3$ (2.1 g), di-(1-naphthylmethyl)acetic acid (1.51 g), and hydroxybenzotriazole (0.6 g) were dissolved in dimethylformamide (20 ml) and cooled to 0°. Dicyclohexylcarbodiimide (0.92 g) was added, and the mixture was allowed to warm slowly to 25° and stir for 24 hours. The mixture was filtered, and the filtrate was extracted with ethyl acetate and water. The organic phase was washed with water, sodium bicarbonate, and brine. The organic phase was dried over sodium sulfate, filtered, and evaporated. The crude product was recrystallized from chloroform to give 1.95 g of product. The residue from the mother liquor was purified by chromatography on silica gel, eluting with CHCl$_3$/EtOAc (3/1). Combining the appropriate fractions gave an additional 0.5 g of product.

DNMA—LYS—STA—NHCH$_2$CH(CH$_3$)CH$_2$CH$_3$

DNMA—LYS(Z)—S-TA—NHCH$_2$CH(CH$_3$)CH$_2$CH$_3$ (1.95 g) was dissolved in methanol (30 ml) and palladium on carbon (20%) 0.2 g was added. The flask was flushed with hydrogen and stirred for six hours. The flask was flushed with nitrogen, and the mixture was filtered. The solvent was evaporated to give 1.6 g of product.

INTERMEDIATES FOR EXAMPLE 12

BOC—CYSTA—NHCH$_2$CH(CH$_3$)CH$_2$CH$_3$

A solution of 6.78 g (21.5 mmole) of BOC—CYSTA and 2.9 g (21.5 mmole) of HOBT in 100 ml DMF was cooled in ice and treated with 4.48 g (21.5 mmole) of DCC followed by 1.88 g (21.5 mmole) of S-(—)-1-amino-2-methylbutane. After stirring at 0° for 0.5 hour, the mixture was allowed to stir at room temperature overnight. The mixture was filtered and the DMF removed under high vacuum. The residue was taken up in EtOAc and washed with 1 N HCl, saturated NaHCO$_3$, then saturated NaCl. Drying and removal of the solvent under reduced pressure gave the crude product as a waxy solid. Chromatography on silica gel, eluting with CHCl$_3$/MeOH (99/1) gave 8.26 g of the pure product. The structure was confirmed by mass spectroscopy.

CYSTA—NHCH$_2$CH(CH$_3$)CH$_2$CH$_3$.HCl

A solution of 8.26 g (21.5 mmole) of BOC—CYS-TA—NHCH$_2$CH(CH$_3$)CH$_2$CH$_3$ in 85 ml of CH$_2$Cl$_2$ was saturated with HCl gas, allowed to stir for 1 hour, then resaturated with HCl gas and allowed to stir for an additional 2 hours. The solution was diluted with Et$_2$O and the white solid collected and washed with Et$_2$O. There was obtained 5.47 g of the product as a white solid. The structure was confirmed by mass spectroscopy.

α-BOC-ε-Z—LYS—CYS-TA—NHCH$_2$CH(CH$_3$)CH$_2$CH$_3$

A solution of 1.7 g (4.5 mmole) of α-BOC-ε-Z—LYS, 1.5 g (4.7 mmole) of CYS-TA—NHCH$_2$CH(CH$_3$)CH$_2$CH$_3$.HCl, and 0.63 g (4.7 mmole) of HOBI in 20 ml DMF was cooled in ice and treated with 0.85 ml (6.1 mmole) of Et$_3$N followed by 0.96 g (4.7 mmole) of DCC. After stirring at 0° for 0.5 hour, the mixture was allowed to stir at room temperature for 2 days. The mixture was filtered and the filtrate diluted with EtOAc and washed with water, saturated NaHCO$_3$, then saturated NaCl. After drying and removal of the solvent under reduced pressure, the crude product was chromatographed on silica gel, eluting with EtOAc/hexane (3/1). There was obtained 2.6 g of the pure product.

ε-Z—LYS—CYSTA—NHCH$_2$CH(CH$_3$)CH$_2$CH$_3$

A solution of 2.6 g (4.0 mmole) of α-BOC-ε-Z—LYS—CYSTA—NHCH$_2$CH(CH$_3$)CH$_2$CH$_3$ in 20 ml of CH$_2$Cl$_2$ was treated with 5 ml of TFA and allowed to stir at room temperature for 5 hours. The solvent was removed under reduced pressure and the residue taken up in EtOAc and washed with saturated NaHCO$_3$, then saturated NaCl. Drying and removal of the solvent under reduced pressure left 2.18 g of the product, sufficiently pure for use in the following step.

DNMA—LYS(Z)—CYS-TA—NHCH$_2$CH(CH$_3$)CH$_2$CH$_3$

A solution of 1.8 g 3.3 mmole) of ε-Z—LYS—CYS-TA—NHCH$_2$CH(CH$_3$)CH$_2$CH$_3$, 1.12 g (3.3 mmole) of di-(1-naphthylmethyl)acetic acid, and 0.45 g (3.3 mmole) of HOBT in 20 ml of DMF was cooled in ice and treated with 0.68 g (3.3 mmole) of DCC. After 0.5 hour at 0°, the mixture was stirred at room temperature overnight. The mixture was filtered and the filtrate diluted with EtOAc and washed with water, saturated NaHCO$_3$, then saturated NaCl. After drying over Na$_2$SO$_4$ and removal of the solvent under reduced pressure, the residue was crystallized from EtOAc to give 2.8 g of product. The structure was confirmed by NMR spectroscopy.

DNMA—LYS—CYSTA—NHCH$_2$CH(CH$_3$)CH$_2$CH$_3$

A solution of 2.8 q (3.2 mmole) of DNMA—LYS(-Z)—CYSTA—NHCH$_2$CH(CH$_3$)CH$_2$CH$_3$ in 30 ml of MeOH was treated with 200 mg of 20% Pd/C and stirred under an atmosphere of hydrogen for 6 hours. The mixture was filtered and the solvent removed under reduced pressure giving 2.0 g of the product. The structure was confirmed by NMR and mass spectroscopy.

INTERMEDIATES FOR EXAMPLE 16

DNMA—LYS—STA—NHCH$_2$CH(CH$_3$)CH$_2$CH$_3$
|
β-ALA—Z

A solution of 1.05 g (4.7 mmole) of Z-β-alanine, 0.64 g (4.7 mmole) of HOBT, and 3.0 g (4.3 mmole) of DNMA—LYS—STA—NHCH$_2$CH(CH$_3$)CH$_2$CH$_3$ in 30 ml DMF was cooled in ice and treated with 0.97 g (4.7 mmole) of DCC in 10 ml DMF. After 0.5 hour at 0°, the mixture was allowed to stir at room temperature for 48 hours. The mixture was filtered and the filtrate removed under high vacuum. The residue was taken up in EtOAc and washed with H$_2$O, saturated NaHCO$_3$, then brine. Drying and removal of the solvent under reduced pressure gave 2.6 g of product. The structure was confirmed by NMR and mass spectroscopy.

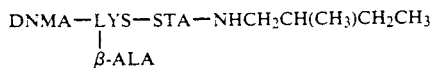

To a solution of 1.7 g (1.9 mmole) of

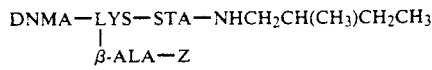

in 40 ml of MeOH was added 0.5 g of 20% Pd/C and the suspension purged with hydrogen for 5 hours. The suspension was filtered and the solvent removed under reduced pressure to give 1.4 g of the product. The structure was confirmed by NMR spectroscopy. The material was of sufficient purity for use in the subsequent reaction.

INTERMEDIATE FOR EXAMPLE 20

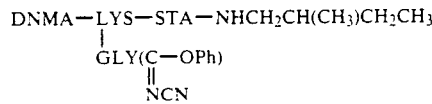

A solution of 2.1 g (2.85 mmole) of

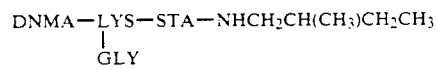

and 0.68 g (2.85 mmole) of diphenoxycarbodiimide in 30 ml of CH$_2$Cl$_2$ was stirred overnight under a nitrogen atmosphere. The solvent was then removed under reduced pressure, and the residue chromatographed on silica gel, eluting with CHCl$_3$/MeOH (96/4). There was obtained 1.1 g of the product. The structure was confirmed by NMR and mass spectroscopy. The material was of sufficient purity for use in the following step.

We claim:

1. A peptide selected from the group consisting of:

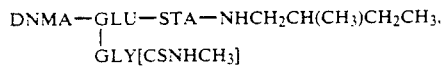

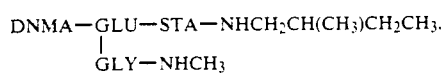

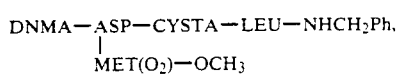

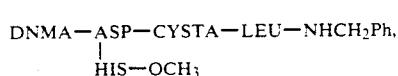

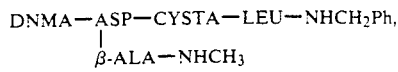

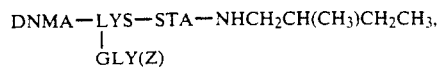

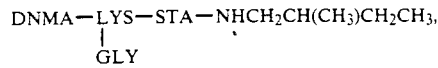

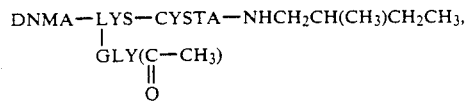

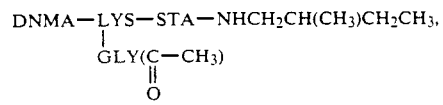

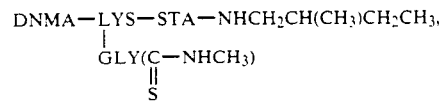

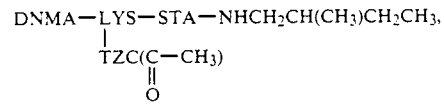

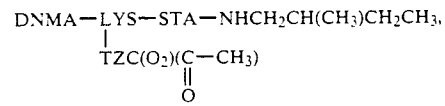

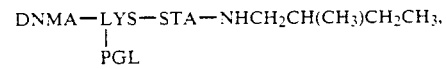

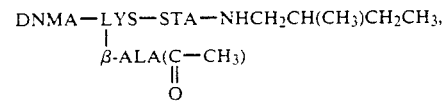

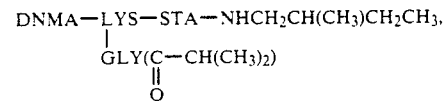

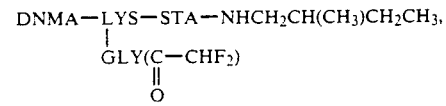

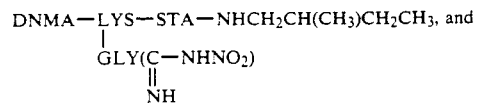

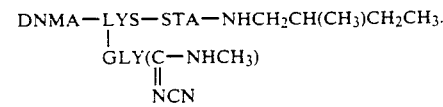

* * * * *